United States Patent
Nishio et al.

(10) Patent No.: US 8,541,615 B2
(45) Date of Patent: Sep. 24, 2013

(54) METHOD FOR PRODUCING BIPHENYLTETRACARBOXYLIC ACID TETRAESTER

(75) Inventors: Masayuki Nishio, Ube (JP); Hiroaki Imajima, Ube (JP); Takato Nakamura, Ube (JP); Yoshihiro Yamauchi, Ube (JP)

(73) Assignee: Ube Industries, Ltd., Ube-shi (JP)

( * ) Notice: Subject to any disclaimer, the term of this patent is extended or adjusted under 35 U.S.C. 154(b) by 299 days.

(21) Appl. No.: 13/057,600

(22) PCT Filed: Aug. 6, 2009

(86) PCT No.: PCT/JP2009/063942
§ 371 (c)(1),
(2), (4) Date: Feb. 15, 2011

(87) PCT Pub. No.: WO2010/016544
PCT Pub. Date: Feb. 11, 2010

(65) Prior Publication Data
US 2011/0137069 A1    Jun. 9, 2011

(30) Foreign Application Priority Data
Aug. 6, 2008    (JP) .................. 2008-203497

(51) Int. Cl.
*C07C 69/604*    (2006.01)

(52) U.S. Cl.
USPC ............................. 560/76; 560/77

(58) Field of Classification Search
USPC ...................................... 560/77, 76
See application file for complete search history.

(56) References Cited

U.S. PATENT DOCUMENTS

| 4,581,469 A | 4/1986 | Itatani et al. |
| 6,914,154 B2 * | 7/2005 | Yamamoto et al. ............ 560/76 |
| 7,271,281 B2 * | 9/2007 | Tsuji et al. ................ 560/76 |
| 2003/0088120 A1 | 5/2003 | Yamamoto et al. |
| 2004/0039222 A1 | 2/2004 | Yamamoto et al. |

FOREIGN PATENT DOCUMENTS

| JP | A-S55-141417 | 11/1980 |
| JP | A-S60-51150 | 3/1985 |
| JP | A-S61-106541 | 5/1986 |
| JP | A-2003-113143 | 4/2003 |
| JP | A-2004-131470 | 4/2004 |
| JP | A-2004-224752 | 8/2004 |

OTHER PUBLICATIONS

Koshimura, et al., "Effect of Substituents on the Keto-Enol Equilibrium of Alkyl-substituted β-Diketones," *Bulletin of the Chemical Society of Japan* (1973) 46:632-634.

International Search Report issued in corresponding PCT Application No. PCT/JP2009/063942, mailed Oct. 6, 2009.

International Preliminary Report on Patentability and Written Opinion in corresponding PCT Application No. PCT/JP2009/063942, mailed Mar. 17, 2011.

Office Action issued in Chinese Patent Application No. 200980139722.2 on Feb. 8, 2013.

* cited by examiner

*Primary Examiner* — Johann R Richter
*Assistant Examiner* — Pancham Bakshi
(74) *Attorney, Agent, or Firm* — Knobbe Martens Olson & Bear LLP

(57) ABSTRACT

Disclosed is a method for producing a biphenyltetracarboxylic acid ester by oxidative coupling a phthalic acid ester by using a catalyst comprising at least a palladium salt, a copper salt and a β-dicarbonyl compound in the presence of a molecular oxygen, wherein the β-dicarbonyl compound is supplied into a reaction mixture liquid intermittently at an interval of less than 30 minutes, or continuously. This method allows, in particular, the selective and economical production of an asymmetric biphenyltetracarboxylic acid tetraester such as 2,3,3',4'-biphenyltetracarboxylic acid tetraester.

10 Claims, No Drawings

METHOD FOR PRODUCING BIPHENYLTETRACARBOXYLIC ACID TETRAESTER

This application is the U.S. National Phase under 35 U.S.C. §371 of International Application No. PCT/JP2009/063942, filed Aug. 6, 2009, designating the U.S., and published in Japanese as WO2010/156544 on Feb. 11, 2010, which claims priority to Japanese Patent Application No. 2008-203497, filed Aug. 6, 2008, the entire contents of which are incorporated herein by reference.

TECHNICAL FIELD

The present invention relates to a more economical production method for selectively producing a biphenyltetracarboxylic acid tetraester, in particular an asymmetric biphenyltetracarboxylic acid tetraester such as 2,3,3',4'-biphenyltetracarboxylic acid tetraester by oxidative coupling a phthalic acid ester by using a catalyst comprising palladium in the presence of a molecular oxygen.

BACKGROUND ART

Some examples have been already known for a production method for selectively producing an asymmetric 2,3,3',4'-biphenyltetracarboxylic acid tetraester (hereafter, it may be abbreviated as a-BPTT) by oxidative coupling a phthalic acid ester by using a catalyst comprising palladium in the presence of a molecular oxygen.

For example, the patent document 1 discloses a production method for producing a-BPTT by oxidative coupling a phthalic acid ester in the presence of an organic palladium salt and an organic copper salt in a reaction liquid under an atmosphere containing a molecular oxygen. Specifically in example 16, 20.4 g of a-BPTT is obtained from the use amount 3.0 mmol of bis(acetylacetonate) palladium chelate salt by a reaction for 7 hours at 140° C. Here, in terms of a turnover number of catalyst (hereafter, it may be abbreviated as TON) represented by {product (mole number)/catalyst palladium (mole number)} for the generation of a-BPTT, the TON of palladium in this method was very low, i.e. about 18, and a considerable amount of valuable noble metal of palladium is consumed. Therefore, this method is economically disadvantageous.

The patent document 2 discloses a method for producing a-BPTT, comprising oxidatively coupling a phthalic acid ester using a palladium salt and a copper salt at a high temperature under an atmosphere in the presence of a molecular oxygen while continuously or intermittently supplementing a β-ketone into a reaction system.

Here, example 1 discloses that the TON regarding the generation of a-BPTT was improved up to about 129; however, the use efficiency of valuable noble metal, palladium was not sufficient, and there was room for further improvements.

In terms of the supplementation of β-diketone in this production method, it is described that preferred is a method of feeding about 1.0 to four-fold moles relative to palladium salt in onset of reaction and then supplementing one to ten times intermittently with a ratio as mentioned above in every about 0.5 to 4 hours passing; or a method continuously supplementing it in a ratio of about 0.5 to three-fold moles per hour relative to palladium salt immediately after the beginning of reaction. However, the manner of supplying β-diketone specifically shown in the example was merely a process of feeding it (as an initial feeding) together with palladium salt in onset of reaction, and subsequently, while heating and reacting at an elevated temperature, supplementing it at 2 hour intervals.

In addition, it is merely explained that the β-diketone in this production method may be those capable of forming a palladium chelate salt. Those shown in the specific examples were only acetylacetone.

The non-patent document 1 investigated the effect of substituent groups on the ratio of enol form in a keto-enol equilibrium of β-diketones; however, it does not mention a role of the β-diketones as a catalytic component.

LIST OF REFERENCES

Patent Documents

Patent document 1: JP-A-1980-141417
Patent document 2: JP-A-1986-106541

Non-Patent Document

Non-patent document 1: *Bull. Chem. Soc. Jpn.* 1973, 46, 632

SUMMARY OF INVENTION

Problems to be Solved by the Invention

The objective of the present invention is to provide an economical and improved production method for selectively producing a biphenyltetracarboxylic acid tetraester, in particular an asymmetric biphenyltetracarboxylic acid tetraester such as 2,3,3',4'-biphenyltetracarboxylic acid tetraester by oxidative coupling a phthalic acid diester by using a catalyst comprising palladium in the presence of a molecular oxygen.

Means for Solving the Problems

The present invention relates to the following items.
1. A method for producing a biphenyltetracarboxylic acid tetraester by oxidative coupling a phthalic acid diester by using a catalyst comprising at least a palladium salt, a copper salt and a β-dicarbonyl compound in the presence of a molecular oxygen, wherein
the β-dicarbonyl compound is supplied into a reaction mixture liquid intermittently at an interval of less than 30 minutes, preferably less than 10 minutes, or continuously.
2. A method for producing a biphenyltetracarboxylic acid tetraester according to the item 1, wherein the β-dicarbonyl compound is supplied into the reaction mixture liquid intermittently or continuously at a temperature of the reaction mixture liquid not lower than 130° C., preferably not lower than 140° C. and more preferably not lower than 150° C.
3. A method for producing a biphenyltetracarboxylic acid tetraester according to the item 1 or 2, wherein 2,3,3',4'-biphenyltetracarboxylic acid tetraester is produced as a product.

Here, the product means a major product, not a by-product.
4. A method for producing a biphenyltetracarboxylic acid tetraester according to any one of the items 1 to 3, wherein a supplied amount of the β-dicarbonyl compound is 0.1 to 50-fold moles, preferably 1 to 10-fold moles, more preferably 2 to 9-fold moles and yet preferably 3 to 8-fold moles per hour relative to one mole of the palladium salt.
5. A method for producing a biphenyltetracarboxylic acid tetraester according to any one of the items 1 to 4, wherein the β-dicarbonyl compound is a compound, which is denoted by a chemical formula (1) described below, and in which a proportion of an enol form is higher than 80%, preferably 85% and more preferably 90% in a measurement at 26° C. in a solution state at a concentration of 0.1 mol/L in dimethyl phthalate ester, Chemical Formula (1)

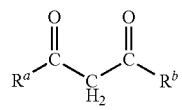

in which $R^a$, $R^b$ are each independently an alkyl group, and they are preferably an alkyl group wherein a total number of carbon atoms in $R^a$ and $R^b$ together is not less than 5 and more preferably 5 to 12.

6. A method for producing a biphenyltetracarboxylic acid tetraester according to any one of the items 1 to 5, wherein the β-dicarbonyl compound is selected from the group consisting of 2,2,6,6-tetramethyl-3,5-heptanedione, 2,6-dimethyl-3,5-heptanedione, 2,8-dimethyl-4,6-nonanedione, 2-methyl-4,6-undecanedione, 2-methyl-4,6-nonanedione, 5,5-dimethyl-2,4-hexanedione, 2,2-dimethyl-3,5-heptanedione, and 5-methyl-2,4-heptanedione.

7. A method for producing a biphenyltetracarboxylic acid tetraester according to any one of the items 1 to 6, wherein a ratio of a used amount of the copper salt to the palladium salt {copper salt (mole number)/palladium salt (mole number)} is in a range of 1 to 10, preferably a range of 3 to 8 and more preferably a range of 4 to 6.

8. A method for producing a biphenyltetracarboxylic acid tetraester according to any one of the items 1 to 7, wherein a TON represented by {product (mole number)/catalyst palladium (mole number)} is not less than 180 and preferably not less than 200.

9. A method for producing a biphenyltetracarboxylic acid tetraester by oxidative coupling a phthalic acid diester by using a catalyst comprising at least a palladium salt, a copper salt and a β-dicarbonyl compound in the presence of a molecular oxygen, wherein the β-dicarbonyl compound is supplied into a reaction mixture liquid intermittently or continuously at a temperature of the reaction mixture liquid not lower than 130° C.

10. A method for producing a biphenyltetracarboxylic acid tetraester by oxidative coupling a phthalic acid diester by using a catalyst comprising at least a palladium salt, a copper salt and a β-dicarbonyl compound in the presence of a molecular oxygen, wherein the β-dicarbonyl compound is a compound, which is denoted by a chemical formula (1) described below, and in which a proportion of an enol form is higher than 80%, preferably 85% and more preferably 90% in a measurement at 26° C. in a solution state at a concentration of 0.1 mol/L in dimethyl phthalate ester, Chemical Formula (1)

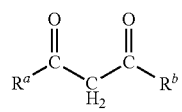

in which $R^a$, $R^b$ are each independently an alkyl group, and they are preferably an alkyl group wherein a total number of carbon of $R^a$ and $R^b$ together is not less than 5 and more preferably 5 to 12.

11. A method for producing a biphenyltetracarboxylic acid tetraester according to the item 10, wherein the β-dicarbonyl compound is selected from the group consisting of 2,2,6,6-tetramethyl-3,5-heptanedione, 2,6-dimethyl-3,5-heptanedione, 2,8-dimethyl-4,6-nonanedione, 2-methyl-4,6-undecanedione, 2-methyl-4,6-nonanedione, 5,5-dimethyl-2,4-hexanedione, 2,2-dimethyl-3,5-heptanedione, and 5-methyl-2,4-heptanedione.

Effect of the Invention

The present invention can provide a more economical production method for selectively producing a biphenyltetracarboxylic acid tetraester, in particular an asymmetric biphenyltetracarboxylic acid tetraester such as 2,3,3',4'-biphenyltetracarboxylic acid tetraester by oxidative coupling a phthalic acid diester by using a catalyst comprising palladium in the presence of a molecular oxygen.

MODE FOR CARRYING OUT THE INVENTION

Hereafter, the present invention is explained in detail.

Specific examples of the phthalic acid diester to be used in the present invention preferably include dimethyl phthalate ester, diethyl phthalate ester, dipropyl phthalate ester, dibutyl phthalate ester, dioctyl phthalate ester, diphenyl phthalate ester and the like. These phthalic acid diesters may be readily obtained by reacting phthalic acid, phthalic anhydride, phthalic halide or the like with a compound having hydroxyl group such as, for example, lower aliphatic alcohol, aromatic alcohol, phenols.

Specific examples of the palladium salt to be used in the present invention includes, for example, palladium chloride, palladium bromide, palladium nitrate, palladium sulfate, palladium hydroxide, palladium acetate, palladium trifluoroacetate, palladium propionate, palladium pivalate, palladium trifluoromethanesulfonate, bis(acetylacetonato)palladium, and bis(1,1,1-5,5,5-hexafluoroacetylacetonato)palladium. Particular preference is given to palladium acetate, palladium propionate, palladium pivalate, palladium trifluoroacetate, palladium hydroxide, and palladium nitrate because they exhibit high catalytic activity.

An amount of the palladium salt to be used is $1 \times 10^{-5}$ to $1 \times 10^{-2}$-fold moles, preferably $5 \times 10^{-5}$ to $5 \times 10^{-4}$-fold moles, more preferably $8 \times 10^{-5}$ to $3 \times 10^{-4}$-fold moles, yet preferably $1 \times 10^{-4}$ to $2 \times 10^{-4}$-fold moles relative to one mole of the phthalic acid diester of a reaction starting material. When palladium is used more than a range of the above condition, the effect of improvement in TON may not be sufficient. On the other hand, when palladium is used less than a range of the above condition, the yield of products per reaction batch may be reduced, which leads the process impractical.

The copper salt to be used in the present invention preferably includes, for example, copper acetate, copper propionate, copper normal-butanoate, copper 2-methylpropionate, copper pivalate, copper lactate, copper butyrate, copper benzoate, copper trifluoroacetate, bis(acetylacetonato)copper, bis(1,1,1-5,5,5-hexafluoroacetylacetonato)copper, copper chloride, copper bromide, copper iodide, copper nitrate, copper nitrite, copper sulfate, copper phosphate, copper oxide, copper hydroxide, copper trifluoromethanesulfonate, copper para-toluenesulfonate, and copper cyanide and the like. Particular preference is given to copper acetate, copper propionate, copper normal-butanoate, copper pivalate, and bis(acetylacetonato)copper due to high effects of promoting the oxidative coupling reaction. Anhydrous copper salts or these hydrates may be preferably used.

An amount of the copper salt to be used is preferably 1 to 10-fold moles, more preferably 3 to 8-fold moles, yet preferably 4 to 6-fold moles relative to one mole of the palladium salt.

In the present invention, both aliphatic and aromatic β-dicarbonyl compounds may be preferably used. Specific examples of the β-dicarbonyl compounds preferably include 1,3-diketones such as acetylacetone, benzoylacetone, trifluoroacetylacetone, 2,4-pentanedione, 2,4-hexanedione, 2,4-heptanedione, 1,3-diphenyl-1,3-propanedione, 1,1,1-trifluoro-2,4-hexanedione; acylacetic acid esters such as methyl acetoacetate, ethyl acetoacetate, methyl 3-oxovalerate; aroylacetic acid esters such as ethyl benzoylacetate; malonic acid esters such as diethyl malonate, Meldrum's acid and the like. Among these, preference is given to 1,3-diketones.

In the present invention, when the β-dicarbonyl compound comprises an aromatic substituent, it is considered that a phthalic acid diester and an aromatic substituent of β-dicarbonyl compound may cause oxidative coupling, which generates a by-product. For this reason, in a more preferred embodiment preference is given to use of a β-dicarbonyl compound not comprising an aromatic substituent but comprising an aliphatic substituent.

As described in the non-patent document 1, a β-dicarbonyl compound may exist in an enol form of a reciprocal isomer with a certain proportion through a keto-enol equilibrium.

The β-dicarbonyl compound to be used in the method for producing biphenyltetracarboxylic acid tetraester of the present invention is preferably the 1,3-diketones denoted by the chemical formula (1) described below which has two protons at α-position wherein substituents are alkyl groups. In addition, it is preferably a compound having a high proportion of enol form, specifically a compound in which a proportion of enol form is higher than 80%, preferably 85% and more preferably 90% in a measurement at 26° C. in a solution state at a concentration of 0.1 mol/L in dimethyl phthalate ester because reaction efficiency and selectivity can be increased, which further increases TON and improves an economical advantage.

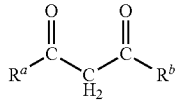

Chemical Formula (1)

in which $R^a$, $R^b$ are each independently an alkyl group, and they are preferably an alkyl group wherein a total number of carbon atoms in $R^a$ and $R^b$ together is not less than 5 and more preferably 5 to 12.

As described in the Summary of the Invention section, the production method using the β-dicarbonyl compound specified here may constitute a preferred embodiment together with other constituents specified in the present invention, or may independently constitute an invention per se.

The β-dicarbonyl compound with a large effect on increase in reaction efficiency may preferably include 2,2,6,6-tetramethyl-3,5-heptanedione (proportion of the enol form: 90.1%), 2,6-dimethyl-3,5-heptanedione (proportion of the enol form: 85.3%) and the like.

On the other hand, the effect on increase in reaction efficiency becomes relatively small if it is a β-dicarbonyl compound such as 3,3-dimethyl-2,4-pentanedione (proportion of the enol form: 0%) incapable of existing in an enol form regarding chemical structure due to lack of proton at α-position, methyl acetoacetate (proportion of the enol form: 6.0%), and acetylacetone (proportion of the enol form: 79.5%) with a relatively small proportion of existence of a enol form.

The non-patent document 1 describes how the proportion of an enol form varies as changing with various substituents in terms of the β-dicarbonyl compounds of the chemical formula (1). The table 1 described below summarized different alkyl groups and proportions of the enol form.

TABLE 1

| Substituent | | Proportion of enol form (%) | [Proportion of enol form of each compound/ Proportion of enol form of acetylacetone] |
|---|---|---|---|
| $R^a$ | $R^b$ | | |
| $CH_3$ | $CH_3$ | 81.2 | 1 |
| $CH_3$ | $C_2H_5$ | 82.1 | 1.01 |
| $CH_3$ | $i$-$C_3H_7$ | 91.6 | 1.13 |
| $CH_3$ | $s$-$C_4H_9$ | 93.4 | 1.15 |
| $CH_3$ | $t$-$C_4H_9$ | 93.7 | 1.15 |
| $CH_3$ | $i$-$C_5H_{11}$ | 91.6 | 1.13 |
| $C_2H_5$ | $C_2H_5$ | 80.0 | 0.99 |
| $C_2H_5$ | $n$-$C_3H_7$ | 85.2 | 1.05 |
| $C_2H_5$ | $i$-$C_3H_7$ | 90.8 | 1.12 |
| $C_2H_5$ | $i$-$C_4H_9$ | 89.2 | 1.10 |
| $C_2H_5$ | $t$-$C_4H_9$ | 93.4 | 1.15 |
| $C_2H_5$ | $i$-$C_5H_{11}$ | 88.5 | 1.09 |
| $n$-$C_3H_7$ | $i$-$C_4H_9$ | 93.7 | 1.15 |
| $i$-$C_3H_7$ | $i$-$C_3H_7$ | 95.8 | 1.18 |
| $n$-$C_4H_9$ | $n$-$C_4H_9$ | 91.7 | 1.13 |
| $i$-$C_4H_9$ | $i$-$C_4H_9$ | 95.3 | 1.17 |
| $t$-$C_4H_9$ | $t$-$C_4H_9$ | 98.0 | 1.21 |
| $n$-$C_5H_{11}$ | $i$-$C_4H_9$ | 94.6 | 1.17 |
| $n$-$C_5H_{11}$ | $n$-$C_5H_{11}$ | 91.7 | 1.13 |

In the present invention, the proportions of enol forms are the values determined by a measurement of a NMR spectrum at 26° C. for a solution at a concentration of 0.1 mol/L in dimethyl phthalate ester, and the proportions of integrated values for protons in a keto form and an enol form on the obtained NMR spectrum.

On the other hand, the proportions of enol forms in the non-patent document 1 (the above table 1) are calculated from a NMR spectrum in a liquid state at 24° C. The proportions of enol forms obtained by these respective measurement methods are different in the absolute value. However, the tendency in the proportions of enol forms (tendency in relative magnitude, order from large to small) is identical to the measurement of the present invention when the measurement was done in the above-mentioned solution of dimethyl phthalate. In any event, it is impossible to measure the proportion of enol form in a compound not being in a liquid state at 24° C. by the measurement method of the non-patent document 1. Therefore, the present invention adopted the proportions of enol forms in a state dissolved in dimethyl phthalate ester, which is closer to the reaction condition.

Namely, as understood from a tendency of the proportion of enol form in the non-patent document 1, in the present invention, more preference is given to a β-dicarbonyl compound exhibiting a higher proportion of enol form than acetylacetone. Specific preference is given to a compound selected from the group consisting of 2,8-dimethyl-4,6-nonanedione (proportion of the enol form: 95.3%, value from the non-patent document; same in the following notes), 2-methyl-4,6-undecanedione (proportion of the enol form: 94.6%), 2-methyl-4,6-nonanedione (proportion of the enol form: 93.7%), 5,5-dimethyl-2,4-hexanedione (proportion of the enol form: 93.7%), 2,2-dimethyl-3,5-heptanedione (proportion of the enol form: 93.4%), and 5-methyl-2,4-heptanedione (proportion of the enol form: 93.4%) due to an enlarged effect on increase in reaction efficiency.

As a result of various investigations by the inventors of the present invention on the β-dicarbonyl compound having a role in the selective production of an asymmetric biphenyltetracarboxylic acid tetraester as a major product in the production method of the present invention, it was revealed that too little β-dicarbonyl compound in a reaction system does not achieve a sufficient effect whereas too much one results in inhibition of reaction. It was also revealed that the amount of a β-dicarbonyl compound present in a reaction system deviates (decreases) due to, for example, vaporization and thermodecomposition during reaction and, thus, it is very important for increasing a reaction efficiency to reduce the deviation of the amount of a β-dicarbonyl compound present in a reaction system (so that the amount of the β-dicarbonyl compound in a reaction system is kept constant) by shortening the interval of supply of the β-dicarbonyl compound.

As a result of various investigations as to a manner of supplying a β-dicarbonyl compound, it was found that a specific feeding method can increase the TON represented by {product (mole number)/catalyst palladium (mole number)} and reduce the consumed amount of valuable noble metal, palladium, leading to an economical production method; and thus, the present invention was attained.

Namely, the production method of the present invention is the method for producing a biphenyltetracarboxylic acid tetraester by oxidative coupling a phthalic acid ester by using a catalyst comprising at least a palladium salt, a copper salt and a β-dicarbonyl compound in the presence of a molecular oxygen, wherein the β-dicarbonyl compound is supplied into a reaction mixture liquid intermittently at an interval of less than 30 minutes, preferably less than 10 minutes, or continuously. As described in the Summary of the Invention section, this production method may constitute a preferred embodiment in combination with other constituents specified in the present invention.

Here, "intermittently or continuously" means intermittent feeding interrupted by an outage period at a given interval and continuous feeding. Namely in a method for producing a biphenyltetracarboxylic acid tetraester by oxidative coupling a phthalic acid ester by using a catalyst comprising at least a palladium salt, a copper salt and a β-dicarbonyl compound in the presence of a molecular oxygen, the present invention is characterized in the β-dicarbonyl compound is supplied into the reaction mixture liquid with an outage period less than 30 minutes (intermittent feeding) to 0 minute (continuous feeding) during the oxidative coupling reaction.

If an interval (outage period) is not less than 30 minutes in supplying a β-dicarbonyl compound, it becomes difficult to reduce an amount of valuable noble metal, palladium to be consumed and the TON represented by {product (mole number)/catalyst palladium (mole number)} decreases, and thus an economical production method is not realized.

The production method of the present invention is also a method for producing a biphenyltetracarboxylic acid ester by oxidative coupling a phthalic acid ester by using a catalyst comprising at least a palladium salt, a copper salt and a β-dicarbonyl compound in the presence of a molecular oxygen, wherein the β-dicarbonyl compound is supplied into a reaction mixture liquid intermittently or continuously at a temperature of the reaction mixture liquid not lower than 130° C. As described in the Summary of the Invention section, this production method may constitute a preferred embodiment in combination with other constituents prescribed in the present invention, or may independently constitute an invention per se.

It is not preferred to initiate the feeding when temperature of the reaction mixture liquid is low because excess of a β-dicarbonyl compound in the reaction system may likely exist without vaporization or decomposition of the β-dicarbonyl compound, which results in inhibition of reaction. In particular, it is not preferred to initiate the reaction at a temperature less than 130° C. at the start of the reaction by heating to an elevated temperature while supplying intermittently or continuously because it may lead to deactivation of a catalyst.

Thus, the temperature to start supplying the β-dicarbonyl compound intermittently or continuously is preferably not lower than 130° C., preferably not lower than 140° C. and more preferably not lower than 150° C. as the temperature of the reaction mixture liquid in the present invention.

While an amount of β-dicarbonyl compound to be supplied may be determined suitably taking effects such as a reaction pressure and a reaction temperature into consideration, preference is usually given to intermittent or continuous feeding with 0.1 to 50-fold moles, preferably 1 to 10-fold moles, more preferably 2 to 9-fold moles and yet preferably 3 to 8-fold moles per hour relative to one mole of palladium salt to be used.

On supplying, the state and form of the β-dicarbonyl compound are not particularly limited. The β-dicarbonyl compound may be intermittently or continuously supplied as such if it is liquid, or a solution of the β-dicarbonyl compound dissolved in, for example, phthalic acid ester of a starting material may be intermittently or continuously supplied into a reaction system by a liquid-feeding pump and the like.

A molecular oxygen may be pure oxygen gas; but by considering risk of explosion, preference is given to use of oxygen-containing mixture gas in which oxygen is diluted to a concentration of about 5% by volume to approximately 50% by volume with inert gas such as nitrogen gas and carbon dioxide gas, or air. For example in case of using air, preference is also given to feeding with a supply rate of about 1 to 20,000 mL/min and particularly 10 to 10,000 mL/min per 1,000 mL of a reaction liquid so as to mix uniformly in a reaction mixture liquid. Specific methods for supplying may preferably include, for example, a method of carrying out gas-liquid contact by passing molecular-oxygen-containing gas along the liquid surface of a reaction mixture liquid, a method of blowing-in by spewing the aforementioned gas from a nozzle placed above the reaction mixture, a method of carrying out gas-liquid contact by supplying the aforementioned gas as bubbles from a nozzle placed at the bottom of the reaction mixture and allowing the bubbles flow through the reaction mixture liquid, a method of supplying the aforementioned gas as bubbles from a perforated plate placed at the bottom of a reaction mixture liquid, or a method of flowing a reaction mixture liquid into a conduit and of spewing the aforementioned gas as bubbles from a lateral side of the conduit into the reaction mixture liquid.

In the present invention, a reaction solvent may be used; but, it may not be used when a reaction starting material is liquid under a reaction condition. From the industrial point, it is preferred that a reaction solvent is not used substantially. When a reaction solvent is used, it may preferably include, for example, an organic ester compound such as ethylene glycol diacetate, dimethyl adipate; a ketone compound such as n-butyl methyl ketone, methyl ethyl ketone, isopropyl ethyl ketone and the like.

There are not particular limitations on a reaction pressure of the production method of the present invention and it may be any condition, that is, under reduced pressure, atmospheric pressure or increased pressure, as long as the catalyst, molecular oxygen and β-dicarbonyl compound can reside in the reaction system in the specified concentration range. Usually, atmospheric pressure is preferred because facilities and operations become simplified.

A reaction temperature in the production method of the present invention is preferably 150 to 220° C., more preferably 170 to 200° C. and yet preferably 180 to 190° C. A reaction time may also be determined appropriately without limitation; but, it is usually 1 to 20 hours and preferably about 5 to 10 hours.

When the present invention is industrially practiced, there is no limitation as to the form of the reaction, and it may be practiced in batch-system or continuous system. In addition, a reactor to be used in the present invention is not particularly limited as long as it is equipped with heating function, stirring function, supplying and discharge function of gas and the like.

EXAMPLES

Next, the production method of the present invention is explained by means of examples and the like. The present invention is not limited with in the following examples.

In the following examples, the products of the oxidative coupling reaction, tetramethyl biphenyltetracarboxylate esters (hereafter, it may be abbreviated as BPTTs) is produced by using dimethyl phthalate ester (hereafter, it may be abbreviated as DMP) as a reaction starting material. Here in accordance with the following calculation equation, the ratio of the isomers, i.e. tetramethyl 3,4,3',4'-biphenyltetracarboxylate ester (hereafter, it may be abbreviated as s-BPTT) and tetramethyl 2,3,3',4'-biphenyltetracarboxylate ester (hereafter, it may be abbreviated as a-BPTT), produced in the products of the oxidative coupling reaction (hereafter, it may be abbreviated as S/A), and the turnover number of catalyst (hereafter, it may be abbreviated as TON) for the major product, a-BPTT were calculated.

$$S/A = \frac{\left(\frac{s\text{-}BPTT}{s\text{-}BPTT + a\text{-}BPTT} \times 100\right)}{\left(\frac{a\text{-}BPTT}{s\text{-}BPTT + a\text{-}BPTT} \times 100\right)}$$

$TON =$ {produced amount of $a\text{-}BPTT$ (mole number)} / {supplied amount of palladium salt (mole number)}

The proportion of enol form was determined from a measurement of a NMR spectrum at 26° C. for a solution at a concentration of 0.1 mol/L in dimethyl phthalate ester, and the proportions of integrated values for the protons in keto form and enol form on the obtained NMR spectrum.

Example 1

The oxidative coupling reaction was carried out in accordance with the following procedure by using a SUS reactor with an inner volume of 1 liter equipped with a stirrer, a conduit for introducing starting materials, a conduit for discharging the product and a conduit for supplying air.

Dimethyl phthalate ester (hereafter, it may be abbreviated as DMP) 3.68 moles were added into the reactor. Palladium acetate 0.54 mmol and acetylacetone copper 3.0 mmol were suspended with DMP 20 mL and added to the reactor. The reaction mixture liquid was bubbled with the air at 390 mL/min and the reaction mixture liquid was heated up to 185° C. at a rate of elevating temperature of 1.64° C./min while it was further stirred by rotating a stirrer at a rotational rate of 400 rpm. From this moment, a solution containing acetylacetone (hereafter, it may be abbreviated as acacH) 30 mmol dissolved in DMP 100 mL was continuously supplied to the reaction mixture liquid at 0.1 mL/min. While keeping the supply, the oxidative coupling reaction was carried out at 185° C. until 6 hours after reaching 185° C.

The total supplied amount of acetylacetone was 12.3 mmol and the supplied amount of DMP was 0.25 moles. The reaction mixture liquid collected after completion of the reaction was 701.3 g due to a lost portion (68.2 g) by taking samples during the course of reaction and further a lost portion released outside system as light volatile. A sample was taken from this reaction mixture liquid, which was diluted with 10 mmol concentration of sodium phosphate buffer solution and acetonitrile to determine the quantity of each product by high performance liquid chromatography (hereafter, it may be abbreviated as HPLC). The total produced amount of a-BPTT was calculated as the produced amount of a-BPTT without taking samples during the course through multiplying the total weight (769.5 g) of the reaction mixture liquid collected after completion of the reaction and the reaction mixture liquid taken as samples during the course of reaction by the percent-by-weight concentration (5.25% by weight) of a-BPTT in the reaction mixture liquid collected after completion of the reaction.

The result was shown in the table 2. TON was 194.

Comparative Example 1

The oxidative coupling reaction was carried out and the quantity of products was determined in a similar manner to example 1 except mere DMP was continuously supplied into the reaction mixture liquid in place of the DMP solution with acacH.

The result was shown in the table 2. TON was 142.

Example 2

The oxidative coupling reaction was carried out and the quantity of products was determined in a similar manner to example 1 except that the supplied rate of the air into the reaction mixture liquid was changed from 390 mL/min to 550 mL/min.

The result was shown in the table 2. TON was 248.

Example 3

The oxidative coupling reaction was carried out and the quantity of products was determined in a similar manner to example 2 except that when the reaction mixture liquid was heated and the temperature reached 140° C., the feeding of the DMP solution with acacH was initiated into the reaction mixture liquid, which was continuously supplied until completion of the reaction.

The result was shown in the table 2. TON was 203.

Comparative Example 2

The oxidative coupling reaction was carried out and the quantity of products was determined in a similar manner to example 2 except that when the reaction mixture liquid was heated and the temperature reached 120° C., the feeding of the DMP solution with acacH was initiated into the reaction mixture liquid, which was continuously supplied until completion of the reaction.

The result was shown in the table 2. TON was 1.

Example 4

The oxidative coupling reaction was carried out at a temperature of 185° C. and the quantity of products was determined in a similar manner to example 2 except that the DMP solution with acacH supplied into the reaction mixture was changed from a solution of acetylacetone 30 mmol and DMP 100 mL to a solution of acetylacetone 60 mmol and DMP 100 mL.

The result was shown in the table 2. TON was 227.

Example 5

The oxidative coupling reaction was carried out at a temperature of 185° C. and the quantity of products was determined in a similar manner to example 2 except that the DMP solution with acacH supplied into the reaction mixture was changed from a solution of acetylacetone 30 mmol and DMP 100 mL to a solution of acetylacetone 15 mmol and DMP 100 mL.

The result was shown in the table 2. TON was 201.

Example 6

The oxidative coupling reaction was carried out at a temperature of 185° C. and the quantity of products was determined in a similar manner to example 6 except that the oxidative coupling reaction was carried out until 8 hours after reaching 185° C., and that the scale of reaction was halved.

The total supplied amount of acetylacetone was 7.4 mmol and the supplied amount of DMP was 0.30 moles. A sample was taken from the reaction mixture liquid, which was diluted with 10 mmol concentration of sodium phosphate buffer solution and acetonitrile to determine the quantity of each product by HPLC.

The result was shown in the table 2. TON was 281.

Example 7

The oxidative coupling reaction was carried out in accordance with the following procedure by using a SUS reactor with an inner volume of 1 liter equipped with a stirrer, a conduit for introducing starting material, a conduit for discharging the product and a conduit for supplying air.

DMP 3.68 moles were added into the reactor. Palladium acetate 0.54 mmol and acetylacetone copper 3.0 mmol were suspended with DMP 20 mL and added to the reactor. The reaction mixture liquid was bubbled with the air at 550 mL/min and the reaction mixture liquid was heated up 185° C. at a rate of elevating temperature of 1.64° C./min while it was further stirred by rotating a stirrer at a rotational rate of 400 rpm. At this point 1.5 g of a solution, which is obtained by dissolving acacH 30 mmol in DMP 100 mL, was supplied to the reaction mixture liquid, and then the oxidative coupling reaction was carried out at a temperature of 185° C. while about 1.4 g (1.2 to 1.6 g) of the aforementioned DMP solution with acacH was intermittently supplied to the reaction mixture liquid in 36 doses in total at an interval of 10 minutes, from 1 hour later to 6 hours later after reaching 185° C.

The total supplied amount of acetylacetone was 11.7 mmol and the supplied amount of DMP was 0.25 moles. A sample was taken from the reaction mixture liquid, which was diluted with 10 mmol concentration of sodium phosphate buffer solution and acetonitrile to determine the quantity of each product by HPLC.

The result was shown in the table 2. TON was 181.

Comparative Example 3

The oxidative coupling reaction was carried out at 185° C. and the quantity of products was determined in a similar manner to example 7 while intermittently supplying the DMP solution with acacH into the reaction mixture liquid 13.5 mL at an interval of 2 hours in 3 doses in total into the reaction mixture liquid in place of supplying it at an interval of 10 minutes from 1 hour later to 6 hours later after reaching 185° C.

The result was shown in the table 2. TON was 137.

TABLE 2

| | Reaction time (hours) | Rate of supplying air per reaction liquid (L/L · min) | Feeding onset temperature of β-dicarbonyl compound (° C.) | Supplied amount of β-dicarbonyl compound based on Pd (fold moles/hour) | Manner of supplying β-dicarbonyl compound | Concentration of a-BPTT in reaction mixture liquid (wt-%) | Produced amount of a-BPTT (g) | TON of a-BPTT | S/A |
|---|---|---|---|---|---|---|---|---|---|
| Example 1 | 6 | 0.65 | 185 | 3.8 | Continuous | 5.25 | 40.4 | 194 | 9/91 |
| Comparative example 1 | 6 | 0.65 | — | — | — | 3.87 | 29.5 | 142 | 9/91 |
| Example 2 | 6 | 0.92 | 185 | 3.7 | Continuous | 6.91 | 51.5 | 298 | 8/92 |
| Example 3 | 6 | 0.92 | 140 | 3.8 | Continuous | 5.53 | 42.6 | 203 | 9/91 |
| Comparative example 2 | 6 | 0.92 | 120 | 4.1 | Continuous | 0.04 | 0.3 | 1 | 21/79 |
| Example 4 | 6 | 0.92 | 185 | 7.4 | Continuous | 6.37 | 47.3 | 227 | 6/94 |
| Example 5 | 6 | 0.92 | 185 | 2.1 | Continuous | 5.62 | 41.9 | 201 | 9/91 |
| Example 6 | 8 | 0.93 | 185 | 3.4 | Continuous | 7.30 | 29.3 | 281 | 10/90 |
| Example 7 | 6 | 0.92 | 185 | 3.6 | Interval of 10 minutes | 5.00 | 37.6 | 181 | 9/91 |
| Comparative example 3 | 6 | 0.92 | 185 | 3.7 | Interval of 120 minutes | 3.79 | 28.4 | 137 | 10/90 |

Example 8

The oxidative coupling reaction was carried out at a temperature of 185° C. in a similar manner to example 2 except that the scale of reaction was decreased by ⅔ times (scale of 2.45 moles for DMP), and that a solution in which 3,5-heptanedione 24 mmol were dissolved in DMP 100 mL was used in place of the solution in which acetylacetone 30 mmol were dissolved with DMP 100 mL.

The total supplied amount of 3,5-heptanedione was 9.2 mmol and the supplied amount of DMP was 0.20 moles. A sample was taken from the reaction mixture liquid, which was diluted with 10 mmol concentration of sodium phosphate buffer solution and acetonitrile to determine the quantity of each product by HPLC.

The result was shown in the table 3. TON was 261.

Example 9

The oxidative coupling reaction was carried out at a temperature of 185° C. in a similar manner to example 8 except that a solution in which benzoylacetone 24 mmol were dissolved in DMP 100 mL was used in place of the solution in which 3,5-heptanedione 24 mmol were dissolved in DMP 100 mL.

The total supplied amount of benzoylacetone was 9.6 mmol and the supplied amount of DMP was 0.21 moles. A sample was taken from the reaction mixture liquid, which was diluted with 10 millimolar concentration of sodium phosphate buffer solution and acetonitrile to determine the quantity of each product by HPLC.

The result was shown in the table 3. TON was 245.

Example 10

The oxidative coupling reaction was carried out at a temperature of 185° C. in a similar manner to example 8 except that a solution in which methyl acetoacetate 24 mmol were dissolved in DMP 100 mL was used in place of the solution in which 3,5-heptanedione 24 mmol were dissolved in DMP 100 mL.

The finally supplied amount of methyl acetoacetate became 9.9 mmol and the supplied amount of DMP did 0.21 moles. A sample was taken from the reaction mixture liquid, which was diluted with 10 mmol concentration of sodium phosphate buffer solution and acetonitrile to determine the quantity of each product by HPLC.

The result was shown in the table 3. TON was 193.

TABLE 3

| Type of β-dicarbonyl compound | Supplied amount of β-dicarbonyl compound based on Pd (fold moles/hour) | Concentration of a-BPTT in reaction mixture liquid (wt-%) | Produced amount of a-BPTT (g) | TON of a-BPTT | S/A |
| --- | --- | --- | --- | --- | --- |
| Comp-Ex 1 | No | — | 3.87 | 29.5 | 142 | 9/91 |
| Ex. 2 | acacH | 3.7 | 6.91 | 51.5 | 248 | 8/92 |
| Ex. 8 | 3,5-Heptanedione | 4.5 | 7.17 | 36.3 | 261 | 8/92 |
| Ex. 9 | Benzoylacetone | 4.5 | 6.85 | 34.0 | 245 | 8/92 |
| Ex. 10 | Methyl acetoacetate | 4.6 | 5.34 | 26.9 | 193 | 12/88 |

Example 11

The oxidative coupling reaction was carried out at a temperature of 185° C. in a similar manner to example 8 except that a solution in which 2,2,6,6-tetramethyl-3,5-heptanedione (hereafter, it may be abbreviated as TMHD) 24 mmol were dissolved in DMP 100 mL was used in place of the solution in which 3,5-heptanedione 24 mmol were dissolved in DMP 100 mL.

The total supplied amount of TMHD was 9.2 mmol and the supplied amount of DMP was 0.20 moles. A sample was taken from the reaction mixture liquid, which was diluted with 10 mmol concentration of sodium phosphate buffer solution and acetonitrile to determine the quantity of each product by HPLC.

The result was shown in the table 4. TON was 294.

Example 12

The oxidative coupling reaction was carried out at a temperature of 185° C. in a similar manner to example 8 except that a solution in which 2,6-dimethyl-3,5-heptanedione 24 mmol were dissolved in DMP 100 mL was used in place of the solution in which 3,5-heptanedione 24 mmol were dissolved in DMP 100 mL.

The total supplied amount of 2,6-dimethyl-3,5-heptanedione was 9.2 mmol and the supplied amount of DMP was 0.20 moles. A sample was taken from the reaction mixture liquid, which was diluted with 10 mmol concentration of sodium phosphate buffer solution and acetonitrile to determine the quantity of each product by HPLC.

The result was shown in the table 4. TON was 265.

TABLE 4

| Type of β-dicarbonyl compound | Proportion of enol form | Supplied amount of β-dicarbonyl compound based on Pd (fold moles/hour) | Concentration of a-BPTT in reaction mixture liquid (wt-%) | Produced amount of a-BPTT (g) | TON of a-BPTT | S/A |
| --- | --- | --- | --- | --- | --- | --- |
| Comp-Ex. 1 | No | No | — | 3.87 | 29.5 | 142 | 9/91 |
| Ex. 2 | acacH | 79.5 | 3.7 | 6.91 | 51.5 | 248 | 8/92 |
| Ex. 10 | Methyl acetoacetate | 6.0 | 4.6 | 5.34 | 26.9 | 193 | 12/88 |

TABLE 4-continued

| | Type of β-dicarbonyl compound | Proportion of enol form | Supplied amount of β-dicarbonyl compound based on Pd (fold moles/hour) | Concentration of a-BPTT in reaction mixture liquid (wt-%) | Produced amount of a-BPTT (g) | TON of a-BPTT | S/A |
|---|---|---|---|---|---|---|---|
| Ex. 11 | TMHD | 90.1 | 4.2 | 8.27 | 41.9 | 294 | 6/94 |
| Ex. 12 | 2,6-dimethyl-3,5-heptane-dione | 85.3 | 4.2 | 7.36 | 36.9 | 265 | 7/93 |

INDUSTRIAL APPLICABILITY

According to the present invention, there is provided an economical and improved production method for selectively producing a biphenyltetracarboxylic acid tetraester, in particular an asymmetric biphenyltetracarboxylic acid tetraester such as 2,3,3',4'-biphenyltetracarboxylic acid tetraester by oxidative coupling a phthalic acid diester by using a catalyst comprising palladium in the presence of a molecular oxygen.

The invention claimed is:

1. A method for producing a biphenyltetracarboxylic acid tetraester comprising oxidatively coupling a phthalic acid diester with a catalyst comprising at least a palladium salt, a copper salt and a β-dicarbonyl compound in the presence of molecular oxygen, wherein
the β-dicarbonyl compound is supplied into a reaction mixture liquid intermittently at an interval of less than 30 minutes, or continuously at a temperature of the reaction mixture liquid not lower than 130° C.

2. A method for producing a biphenyltetracarboxylic acid tetraester according to claim 1, wherein 2,3,3',4'-biphenyltetracarboxylic acid tetraester is produced as a product.

3. A method for producing a biphenyltetracarboxylic acid tetraester according to claim 1, wherein a supplied amount of the β-dicarbonyl compound is 0.1 to 50-fold moles per hour relative to one mole of the palladium salt.

4. A method for producing a biphenyltetracarboxylic acid tetraester according to claim 1, wherein the β-dicarbonyl compound is denoted by a chemical formula (1), and in which a proportion of an enol form is higher than 80% at 26° C. in a solution state at a concentration of 0.1 mol/L in dimethyl phthalate ester,

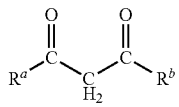

Chemical Formula (1)

in which $R^a$, $R^b$ are each independently an alkyl group.

5. A method for producing a biphenyltetracarboxylic acid tetraester according to claim 1, wherein the β-dicarbonyl compound is selected from the group consisting of 2,2,6,6-tetramethyl-3,5-heptanedione, 2,6-dimethyl-3,5-heptanedione, 2,8-dimethyl-4,6-nonanedione, 2-methyl-4,6-undecanedione, 2-methyl-4,6-nonanedione, 5,5-dimethyl-2,4-hexanedione, 2,2-dimethyl-3,5-heptanedione, and 5-methyl-2,4-heptanedione.

6. A method for producing a biphenyltetracarboxylic acid tetraester according to claim 1, wherein a ratio of the copper salt to the palladium salt {copper salt (mole number)/palladium salt (mole number)} is in a range of 1 to 10.

7. A method for producing a biphenyltetracarboxylic acid tetraester according to claim 1, wherein a TON represented by {product (mole number)/catalyst palladium (mole number)} is not less than 180.

8. A method for producing a biphenyltetracarboxylic acid tetraester comprising oxidatively coupling a phthalic acid diester with a catalyst comprising at least a palladium salt, a copper salt and a β-dicarbonyl compound in the presence of molecular oxygen, wherein
the β-dicarbonyl compound is supplied into a reaction mixture liquid intermittently or continuously at a temperature of the reaction mixture liquid not lower than 130° C.

9. A method for producing a biphenyltetracarboxylic acid tetraester comprising oxidatively coupling a phthalic acid diester with a comprising at least a palladium salt, a copper salt and a β-dicarbonyl compound in the presence of molecular oxygen, wherein
the β-dicarbonyl compound is a compound denoted by a chemical formula (1), and in which a proportion of an enol form is higher than 80% at 26° C. in a solution state at a concentration of 0.1 mol/L in dimethyl phthalate ester,

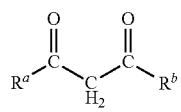

Chemical Formula (1)

wherein $R^a$, $R^b$ are each independently an alkyl group wherein the β-dicarbonyl compound is supplied into a reaction mixture liquid intermittently or continuously at a temperature of the reaction mixture liquid not lower than 130° C.

10. A method for producing a biphenyltetracarboxylic acid tetraester according to claim 9, wherein the β-dicarbonyl compound is selected from the group consisting of 2,2,6,6-tetramethyl-3,5-heptanedione, 2,6-dimethyl-3,5-heptanedione, 2,8-dimethyl-4,6-nonanedione, 2-methyl-4,6-undecanedione, 2-methyl-4,6-nonanedione, 5,5-dimethyl-2,4-hexanedione, 2,2-dimethyl-3,5-heptanedione, and 5-methyl-2,4-heptanedione.

* * * * *